(12) United States Patent
Frostaa et al.

(10) Patent No.: US 10,369,268 B2
(45) Date of Patent: Aug. 6, 2019

(54) ANAL IRRIGATION SYSTEM

(71) Applicant: Coloplast A/S, Humlebaek (DK)

(72) Inventors: Isak Frostaa, Malmoe (SE); Hans Falleboe, Gentofte (DK); Richard Morgan Hickmott, Helsingoer (DK); Niels Hvid, Vedaek (DK)

(73) Assignee: Coloplast A/S, Humlebaek (DK)

( * ) Notice: Subject to any disclaimer, the term of this patent is extended or adjusted under 35 U.S.C. 154(b) by 46 days.

(21) Appl. No.: 15/512,086

(22) PCT Filed: Sep. 21, 2015

(86) PCT No.: PCT/DK2015/050285
§ 371 (c)(1),
(2) Date: Mar. 17, 2017

(87) PCT Pub. No.: WO2016/041564
PCT Pub. Date: Mar. 24, 2016

(65) Prior Publication Data
US 2017/0252506 A1    Sep. 7, 2017

(30) Foreign Application Priority Data

Sep. 19, 2014 (DK) .................................. 2014 00536

(51) Int. Cl.
*A61M 3/02* (2006.01)

(52) U.S. Cl.
CPC ........ *A61M 3/0258* (2013.01); *A61M 3/0208* (2014.02); *A61M 3/0245* (2013.01); *A61M 3/0295* (2013.01); *A61M 2205/502* (2013.01); *A61M 2210/1067* (2013.01)

(58) Field of Classification Search
CPC .... A61M 3/0258; A61M 3/0295; A61M 3/02; A61M 3/0208; A61M 3/0233; A61M 3/0254; A61M 3/0266; A61M 3/00; A61M 2210/1067; A61M 5/00; A61M 3/0279; A61M 3/0245; A61M 2205/502; A61M 2205/505; A61M 2205/52; A61M 2205/50

See application file for complete search history.

(56) References Cited

U.S. PATENT DOCUMENTS

| | | | |
|---|---|---|---|
| 1,352,306 | A | 9/1920 | Mott |
| 1,484,621 | A | 2/1924 | Bond et al. |
| 3,398,743 | A | 8/1968 | Shalit |
| 3,794,031 | A | 2/1974 | Bloom |
| 3,888,235 | A | 6/1975 | May et al. |
| 4,014,322 | A | 3/1977 | Shah |
| 4,828,546 | A | 5/1989 | McNeil et al. |
| 5,201,893 | A | 4/1993 | Holloway et al. |
| 5,386,735 | A | 2/1995 | Langdon |
| 5,505,707 | A | 4/1996 | Manzie et al. |

(Continued)

FOREIGN PATENT DOCUMENTS

| | | |
|---|---|---|
| BE | 503877 A | 6/1951 |
| CN | 2160402 Y | 4/1994 |

(Continued)

*Primary Examiner* — Kami A Bosworth
*Assistant Examiner* — Alexandra Lalonde
(74) *Attorney, Agent, or Firm* — Coloplast Corp., Coloplast A/S; Nick Baumann

(57) ABSTRACT

An anal irrigation system including a control unit (2) is provided. The control unit (2) is connected to an external tube (4) by an extension cord (9), so that pivoting of the control unit (2) with respect to the external tube (4) is possible.

9 Claims, 3 Drawing Sheets

(56) References Cited

U.S. PATENT DOCUMENTS

| | | | |
|---|---|---|---|
| 6,106,506 A * | 8/2000 | Abell | A61M 3/0258 |
| | | | 604/257 |
| 6,264,636 B1 | 7/2001 | Holm et al. | |
| 6,391,010 B1 | 5/2002 | Wilcox | |
| 7,717,325 B2 | 5/2010 | Puls et al. | |
| 2003/0073963 A1 | 4/2003 | Falconer | |
| 2005/0215961 A1 | 9/2005 | Romano et al. | |
| 2006/0009732 A1 | 1/2006 | Hardy | |
| 2010/0063436 A1* | 3/2010 | Tanghoej | A61M 3/0254 |
| | | | 604/28 |
| 2010/0204681 A1* | 8/2010 | Luther | A61M 3/0262 |
| | | | 604/540 |
| 2014/0005602 A1* | 1/2014 | Andreen | A61M 3/0258 |
| | | | 604/98.02 |

FOREIGN PATENT DOCUMENTS

| | | |
|---|---|---|
| CN | 2892097 Y | 4/2007 |
| DE | 202005016774 U1 | 3/2006 |
| EP | 2679259 A1 | 1/2014 |
| FR | 1222961 A | 6/1960 |
| FR | 2307989 A1 | 11/1976 |
| FR | 2711316 A1 | 4/1995 |
| FR | 2750855 A1 | 1/1998 |
| GB | 06031 | 1/1912 |
| GB | 19107 | 8/1913 |
| GB | 137316 A | 3/1921 |
| WO | 88/00840 A1 | 2/1988 |
| WO | 94/14045 A1 | 6/1994 |
| WO | 9838109 A1 | 9/1998 |
| WO | 03/030969 A1 | 4/2003 |
| WO | 03030968 A1 | 4/2003 |
| WO | 04050534 A2 | 6/2004 |
| WO | 2005/011776 A1 | 2/2005 |
| WO | 2008060902 A1 | 5/2008 |
| WO | 2008060903 A2 | 5/2008 |
| WO | 2009153973 A1 | 12/2009 |
| WO | 2014001313 A1 | 1/2014 |

\* cited by examiner

ANAL IRRIGATION SYSTEM

The invention relates to an anal irrigation system including a control unit attached to the system through an extension cord.

SUMMARY OF THE INVENTION

An anal irrigation system with a control unit for controlling an electrical pump and valves in the system is provided. The control unit is attached to an external tube through an extension cord that allows pivoting of the control unit with respect to the external tube. Other systems having the control unit attached directly to the tube will lead to a bulky control unit and the user might further have to twist the entire system—or at least a major part of the tube—to be able to handle and see the control unit properly.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE INVENTION

Figure 1:
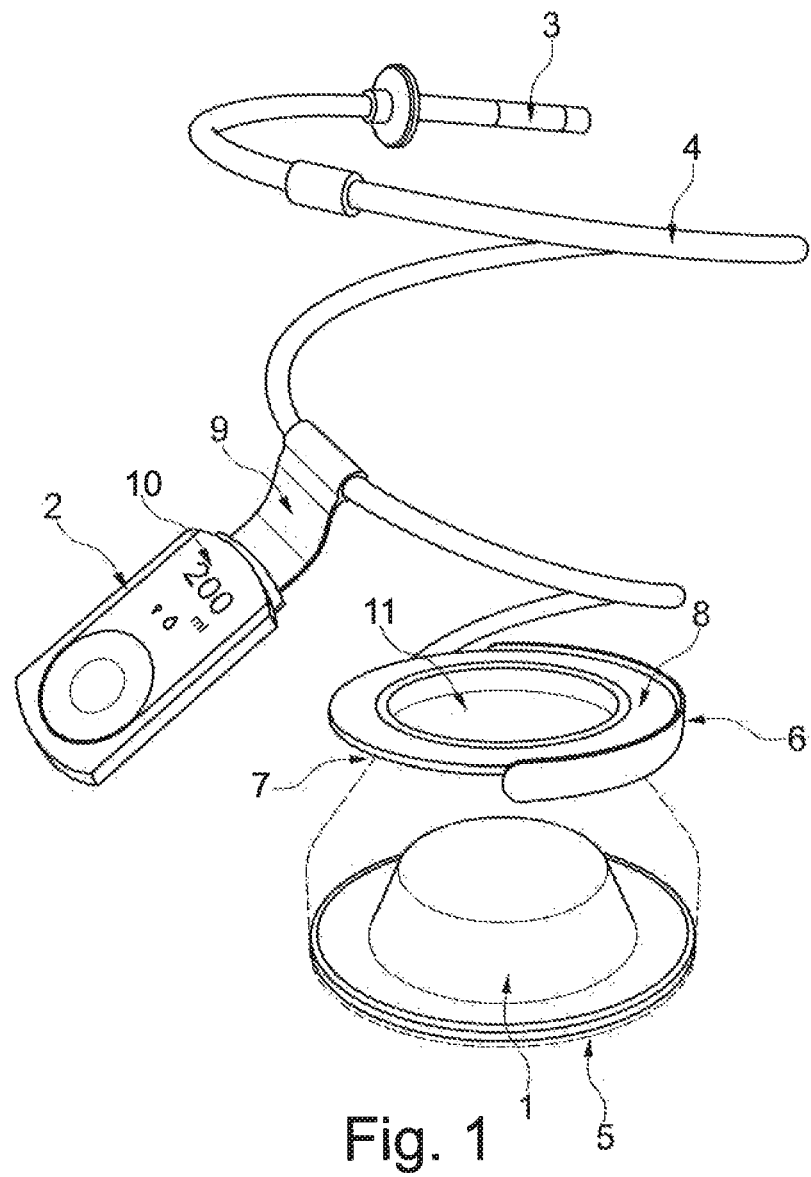
FIG. 1 illustrates an anal irrigation system including a control unit.

Anal irrigation is one of a number of treatments used to aid people with bowel problems. People suffering from bowel problems are often paralyzed, typically due to spinal cord injuries, and confined to a wheelchair or hospitalized. In these situations, often the peristaltic functions, i.e. the reflexes and muscles of the bowel, cannot be stimulated correctly. This results in constipation or random discharge of bowel contents. By using anal irrigation, a stimulation of the peristaltic movements of the colon can be provided. To perform such anal irrigation, a device comprising an anal probe, also called an anal catheter, rectal catheter or speculum, is provided. The anal probe is inserted into the rectum through the anus. The anal probe is typically retained in the rectum by retention means, most commonly a balloon, which is inflated against the wall of the rectum. A liquid, such as water or a saline solution, is then introduced into the rectum through the anal probe. The amount of liquid is generally up to 1.5 liters, depending on the person.

Embodiments relates to an irrigation system comprising a container, tubes, an anal probe, an electrical pump and a control unit, one of the tubes being an external tube connecting the container with the control unit and the anal probe, the control unit being connected to the external tube through an extension cord so that the control unit extends transversely to the external tube, the extension cord including only the electrical wiring, the extension cord allowing for pivoting of the extension cord with respect to the external tube.

Positioning of the control unit transverse to the external tube allows the user to see the text and numbers correctly on the display, when the external tube extends across the thigh of the user during use of the system.

The extension cord allows the control unit to be separated from the lumens in the external tube that includes the liquid, only the electrical wires go through the extension cord. This will lead to a less bulky control unit.

Pivoting of the extension cord with respect to the external tube is advantageous, because it allows pivoting of the control unit with respect to the external tube—thereby enabling the user to see the display without having to twist the external tube.

In the following, whenever referring to a proximal end of an element of the anal probe, the referral is to the end adapted for insertion. Whenever referring to the distal end of an element, the referral is to the end opposite the insertion end. In other words, the proximal end is the end closest to the user, when the anal probe is to be inserted and the distal end is the opposite end—the end furthest away from the user when the anal probe is to be inserted.

The longitudinal direction is the direction from the distal to the proximal end. The transverse direction is the direction perpendicular to the longitudinal direction, which corresponds to the direction across the shaft of the anal probe.

An irrigation system typically comprises a reservoir or container for irrigation liquid, an anal probe and tubing connecting those two. The system also includes a pump for pumping the irrigation liquid into the intestines. If the anal probe is provided with inflatable retention means, a pump for inflating these retention means may also be provided. Alternatively, a system for switching the pumping between pumping irrigation liquid into the intestines and inflating the retention means may be included in the system.

The anal probe comprises a main tubular part, typically called a shaft, extending from the distal end to the proximal end. The tip is positioned in the proximal end of the anal probe and is provided as a rounded closed end of the shaft. The anal probe may comprise a connector in the distal end and may, in an embodiment, comprise a flared end of the catheter so that the diameter of the connector increases with respect to the tubular part.

Usually anal probes used for anal irrigation are approximately 10-20 mm in diameter. The anal probe will typically be provided with eyelets in the proximal end, the eyelets communicating with an irrigation channel inside the anal probe, so that irrigation liquid pumped into the anal probe in the distal end can exit the catheter through the eyelets at the proximal end. The anal probe will also typically be provided with a retention element, e.g. in form of an inflatable balloon, for retaining the anal probe inside the rectum during the irrigation procedure. For the purpose of inflating the balloon, the anal probe is provided with an inflation channel inside the anal probe, the inflation channel extending from the distal end of the anal probe and terminating under the balloon.

The external tube may be only one tube including several lumens—or it may be in the form of two separate tubes, in which case both tubes may extend from the container to the anal probe, one communicating with the inflation channel in the anal probe and one communicating with the irrigation channel in the anal probe. In that case, either of these two tubes may include the electric wire for connecting the control unit with the pump and valves inside the container—and the extension cord will be attached to this tube.

The extension cord at the control unit provides for a pivoting effect of the control unit with respect to the tube connecting the container with the probe. In an example, this pivoting or hinging effect is obtained by providing the extension cord in a material that is flexible, e.g. silicone.

Furthermore, the extension cord may be made as a tube element connected with a strip of silicone material. The tube element may then enclose the external tube and allow for pivoting or hinging the extension cord with respect to the external tube.

In an embodiment, the tube extending from the control unit to the container has three lumens, two for liquid and one for an electrical wire and the tube extending from the control unit to the anal probe has two liquid lumens.

This will allow for an easy and simple configuration of the tubes.

In an embodiment, the container further has a lid with a cavity with room for the control unit, the cavity having a rim that cooperates with a cam on the extension cord.

The hinging effect allows the control unit to be "clicked" into position in a cavity in the lid by a cam cooperating with a rim on the lid.

DETAILED DESCRIPTION OF THE DRAWING

Embodiments, and features of the various exemplary embodiments described in this application, may be combined with each other ("mixed and matched"), unless specifically noted otherwise.

FIG. 1 illustrates an embodiment of an irrigation system. The system includes a container 1, a control unit 2 and a probe 3. Furthermore, there is an external tube 4 connecting the container 1 with the probe 3. The container has a bottom 5 and a top 6, the top 6 has a neck part 7 provided with a lid 8. The control unit is connected to the external tube 4 through an extension cord 9. This extension cord 9 is flexible and allows the control unit 2 to be pivoted with respect to the external tube 4.

The control unit is provided with a display 10, displaying e.g. the actual step during the irrigation procedure. For example, when the balloon is being inflated, the display might show "inflate balloon". Likewise, the display 10 may show the temperature of the irrigation liquid, which preferably should be around 37° C.

Figure 2:
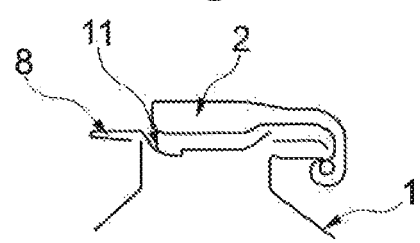
FIG. 2 illustrates how the lid can provide a cavity for storing the control unit.

The external tube 4 may be coiled up around the neck part 7, when the system is stored. In this position, the control unit 2 may be stored in a cavity 11 in the lid 8 as indicated in FIG. 2.

When the user wants to use the system, the control unit 2 can be pivoted so that the display 10 can be seen. Then the user can remove the lid 8 and fill the container 1 with irrigation liquid (e.g. water including a saline solution). During the filling process, the user can see the temperature of the irrigation liquid that is tracked through a temperature sensor in the container (not shown) on the display 10.

When the container is filled with irrigation liquid, the user can move the system to the near vicinity of the toilet and prepare for the irrigation procedure to take place. When the user has positioned himself on the toilet, the tube can be un-coiled from the neck part of the container and the tube, including the control unit can be placed across the user's thigh. Also in this position, and due to the pivoting ability of the extension cord, the control unit may easily be positioned so that the display on the control unit is clearly visible to the user. The user may then be guided by the display to use the control unit to perform the actual irrigation procedure.

Figure 3:
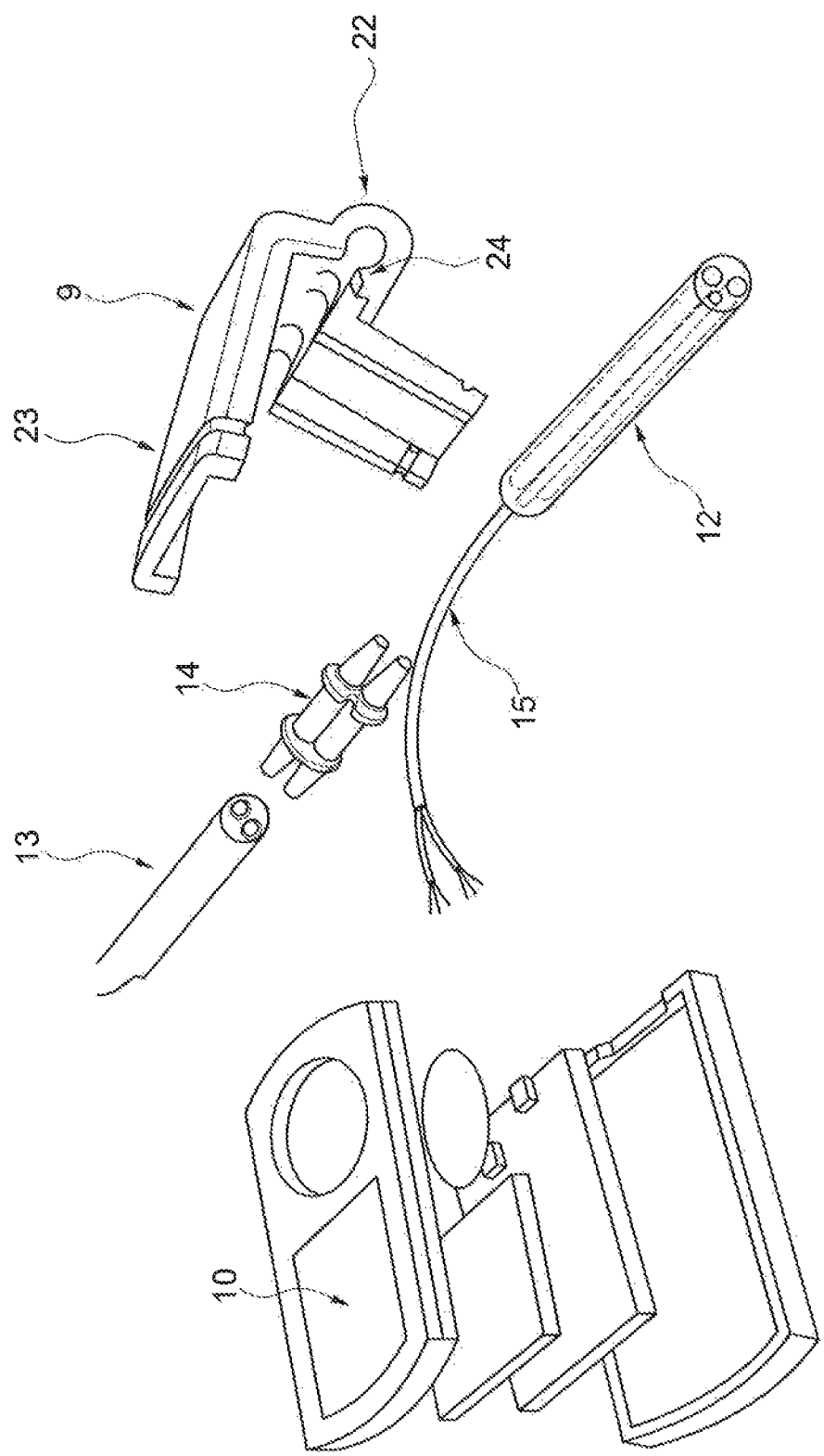
FIG. 3 illustrates an exploded view of the parts of the extension cord for the control unit.
Figures 4, 5:
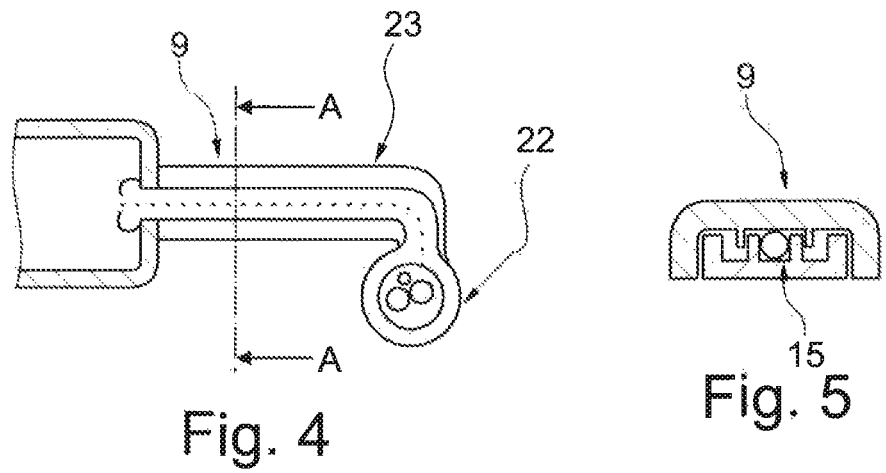
FIG. 4 illustrates a side view of the extension cord.
FIG. 5 illustrates a cross-sectional view of the extension cord.
Figure 6:
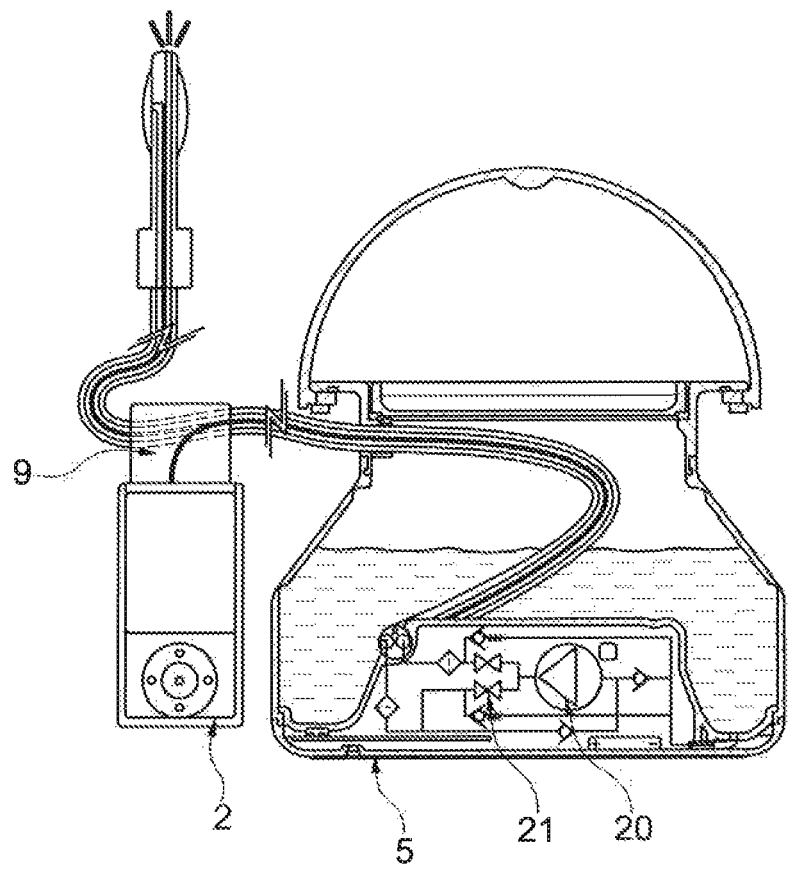
FIG. 6 illustrates an anal irrigation system including a control unit and an electrical pump and valves.

FIGS. 3, 4 and 5 show in detail the connection of the control unit 2 with the external tube 4 through the extension cord 9. In the embodiment shown, the external tube 4 has a first part 12 and a second part 13 connected through a connecting part 14. This allows the tube to be split between a three-lumen tube, the first part 12, from the container to the control unit 2 and a two-lumen tube, the second part 13, from the control unit to the anal probe. The three lumens provides two liquid lumens, one for inflating the balloon and one for irrigation liquid as well as a lumen for the electrical wiring between the control unit and an electrical pump and valves that may be positioned at the bottom of the container. The extension cord illustrated in this embodiment has a tube element 22 with a strip 23 of flexible material, e.g. silicone. The tube element 22 is closeable around the connecting part 14 through a hinge 24. An embodiment of the irrigation system with the pump 20 and valves 21 positioned at the bottom 5 of the container is shown in FIG. 6. The two lumens provides for the two liquid lumens. FIG. 3 illustrate the extension cord in an open position—that is prior to assembling it with the connecting part 14 enclosed and the electrical wiring inside the cord. FIGS. 4 and 5 illustrate a side view (FIG. 4) and a cross-sectional view of section A-A (FIG. 5) of the extension cord 9, when the system is assembled. The electrical wiring 15 is visible in FIGS. 3 and 5.

The invention claimed is:

1. An irrigation system comprising:
    a container having a reservoir space adapted to contain a volume of a liquid and an electrical pump isolated from the reservoir space;
    a connector longitudinally connected between a first tube that is coupled with the container and a second tube that is coupled to an anal probe, with the first tube including a first lumen adapted to transport the liquid and a second lumen including electrical wiring that is connected to the electrical pump; and
    a control unit electrically connected to the electrical pump through connection with the electrical wiring, where the control unit is coupled to the connector by a cord having a hinge;
    wherein the cord couples the control unit to the first tube and to the second tube with the control unit disposed transverse relative to the connector;
    wherein the cord allows the control unit to pivot relative to the first tube and to the second tube;
    wherein the cord has a tube element adapted to close around the connector and a flexible strip of material extending from the tube element, where the flexible strip of material is adapted to allow the control unit to move relative to the second tube that is coupled to the anal probe.

2. The irrigation system of claim 1, wherein the first tube has a third lumen adapted to transport the liquid and the second tube has two lumens, with each of the two lumens adapted to transport the liquid.

3. The irrigation system of claim 1, further comprising a lid that is attachable to the container, where the lid includes a recessed cavity that is sized to receive the control unit.

4. The irrigation system of claim 3, wherein the recessed cavity of the lid has a rim that is adapted to engage the control unit to allow the control unit to be positioned in the lid.

5. The irrigation system of claim 1, wherein the anal probe is sized for insertion into a rectum through an anus of a user, and the anal probe includes an inflation balloon that is inflatable to retain the anal probe in the rectum.

6. The irrigation system of claim 1, wherein the control unit includes a display that is adapted to display information related to transportation of the liquid though the anal probe.

7. The irrigation system of claim 1, wherein the tube element is sized to longitudinally receive the first tube that is coupled with the container, and the hinge allows the tube element to be closed around the connector that is longitudinally connected between the first tube and the second tube.

8. The irrigation system of claim 1, wherein the cord couples the control unit perpendicular relative to the first tube and to the second tube at a location of the connector.

9. The irrigation system of claim 1, where the cord allows the control unit to pivot relative to the first tube and to the second tube without twisting the second tube that is coupled to the anal probe.

* * * * *